United States Patent [19]

Marutani et al.

[11] Patent Number: 5,117,040
[45] Date of Patent: May 26, 1992

[54] ALPHA CRYSTALS OF TETRAKIS[3-(3,5-DI-TERT-BUTYL-4-HYDROXYPHENYL)PROPIONYLOXYMETHYL]METHANE WHICH HAVE GOOD FLOWABILITY AND METHOD OF PRODUCING SAME

[75] Inventors: Masayoshi Marutani, Chikiyo; Fumihide Izumi; Kunihide Oka, both of Nakatsu, all of Japan

[73] Assignee: Yoshitomi Pharmaceutical Industries, Ltd., Osaka, Japan

[21] Appl. No.: 533,531

[22] Filed: Jun. 5, 1990

[30] Foreign Application Priority Data

Jun. 8, 1989 [JP] Japan .................................. 1-145825

[51] Int. Cl.⁵ .............................................. C07C 69/76
[52] U.S. Cl. ............................................................ 560/75
[58] Field of Search ............................................. 560/75

[56] References Cited

U.S. PATENT DOCUMENTS

| 3,962,313 | 6/1976 | Dexter et al. | 260/473 |
| 4,405,807 | 9/1983 | Hasui et al. | 560/75 |
| 4,618,700 | 10/1986 | Gubler et al. | 560/67 |
| 4,739,102 | 4/1988 | Tokunaga | 560/75 |

FOREIGN PATENT DOCUMENTS

| 358157 | 3/1990 | European Pat. Off. |
| 60-13018 | 4/1985 | Japan . |
| 1081789 | 8/1967 | United Kingdom . |

*Primary Examiner*—Paul J. Killos
*Attorney, Agent, or Firm*—Wenderoth, Lind & Ponack

[57] ABSTRACT

The invention provides alpha crystals of tetrakis[3-(3,5-di-tert-butyl-4-hydroxyphenyl)propionyloxymethyl]methane that occur as round granular crystals with high purity, uniform grain size, narrow grain size distribution and good flowability.

3 Claims, 5 Drawing Sheets

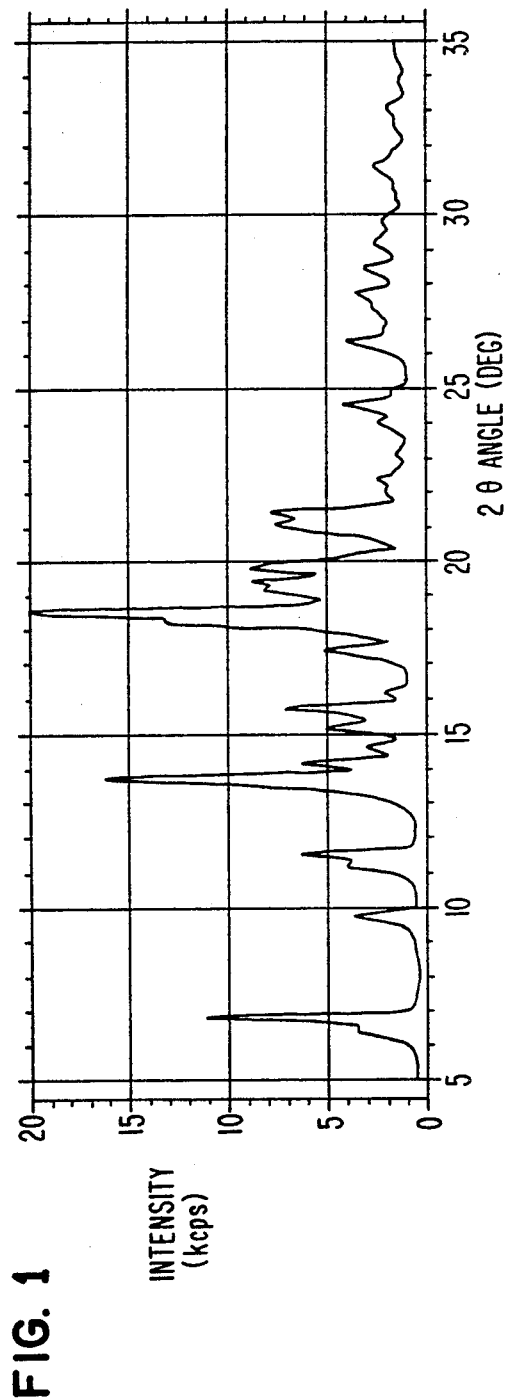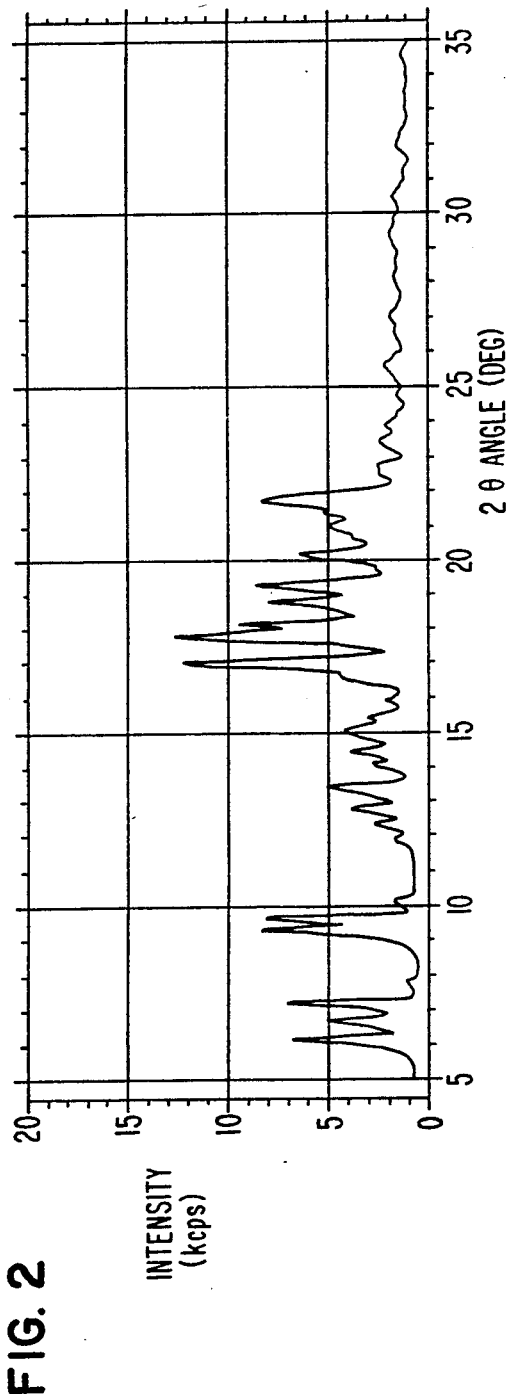

ALPHA CRYSTALS OF TETRAKIS[3-(3,5-DI-TERT-BUTYL-4-HYDROXYPHENYL) PROPIONYLOXYMETHYL]METHANE WHICH HAVE GOOD FLOWABILITY AND METHOD OF PRODUCING SAME

BACKGROUND OF THE INVENTION

This invention relates to novel alpha-form crystals of tetrakis[3-(3,5-di-tert-butyl-4-hydroxyphenyl)propionyloxymethyl]methane which have good flowability and to a method of producing the same. The compound mentioned above is in wide use as an antioxidant for polyolefins and so forth.

The tetrakis[3-(3,5-di-tert-butyl-4-hydroxyphenyl)propionyloxymethyl]methane products that are on the market are in the form of fine powders and, therefore, have problems from the working environment, operation efficiency and measurability viewpoints. Thus, for example, they are readily scattered upon handling, have poor flowability and tend to adhere to containers. An improved product is desired.

Crystallographically, tetrakis[3-(3,5-di-tert-butyl-4-hydroxyphenyl)propionyloxymethyl]methane shows the property so called polymorphism. Thus it can occur in various stable or metastable crystal forms though, chemically, they have one and the same structural formula. The crystal forms so far known include the alpha ($\alpha$), beta ($\beta$), gamma ($\gamma$) and delta ($\delta$) forms, among others.

Among these, the alpha crystal form belongs to the class of stable crystal forms. However, Japanese Patent Publication No. 13018/1985 describes the finding that while said form can be obtained with a slight loss in the step of recrystallization or, in other words, in high yields, said form cannot meet either of the requirements that it should be a powder having good properties and that it should have a high purity.

The present inventors checked the examples disclosed in Japanese Patent Publications Nos. 18617/1967 and 19083/1967 and Japanese Kokai Tokkyo Koho No. 156645/1985 by carrying out recrystallization experiments using n-heptane, n-hexane, methanol and the like. The results may be summarized as follows. The alpha crystals obtained with n-heptane or n-hexane have fairly improved flowability but have a yellow color, hence a low purity, without any marked purification efficiency. These solvents are low-boiling hydrocarbon solvents and therefore require a measure for static electricity and a special filter for solid-liquid separation, among others. Therefore, the method cannot be said to be suited for industrial application. On the other hand, methanol produces an outstanding purification effect, giving alpha crystals satisfactory from both the color and purity viewpoints. However, the product occurs as a fine powder. Therefore, none of the known methods can solve the drawbacks of the products currently on the market to give a desirable product.

As mentioned above, powder products have problems with respect to handling properties, continuous process operability and process automation, for instance. Therefore, various proposals have been made to improve the drawbacks of the currently available products. For example, a means is available which comprises avoiding the use of alpha crystals of tetrakis[3-(3,5-di-tert-butyl-4-hydroxyphenyl)propionyloxymethyl]methane which are poor in purity and flowability and producing delta crystals, or beta crystals unstable from the crystal structure viewpoint. Japanese Patent Publications Nos. 13017/1985 and 13018/1985 propose delta crystals, which have good flowability. However, there are still problems. For instance, in the step of transesterification reaction, (1) addition is required of a particular compound, dimethyl $\beta$-(3,5-di-tert-butyl-4-hydroxybenzyl)glutarate and (2) it is necessary that a molecular adduct with isopropanol should be prepared and, after solid-liquid separation and drying, be crystallized using methanol, ethanol or the like. Japanese Kokai Tokkyo Koho No. 258343/1987 proposes beta crystals having good flowability. However, the method of producing them have some problems. For example, the presence of the starting material methyl 3-(3,5-di-tert-butyl-4-hydroxyphenyl)propionate and an intermediate, namely the tris substituted product, is required before crystallization, making the process complicated, causing a tendency toward decreased product purity and lowering the crystallization yield. The method cannot be said to be economical or suited for industrial application.

SUMMARY OF THE INVENTION

It is an object of the invention to provide alpha crystals of tetrakis[3-(3,5-di-tert-butyl-4-hydroxyphenyl)propionyloxymethyl]methane which have good flowability, high purity and stable crystal structure as well as an improved method of producing the same.

BRIEF DESCRIPTION OF THE DRAWINGS

FIG. 1 shows an X ray diffraction spectrum of the compound of the invention as obtained in Example 1.

FIG. 2 shows an X ray diffraction spectrum of the commercial product used in Example 1.

DETAILED DESCRIPTION

Figure 3:
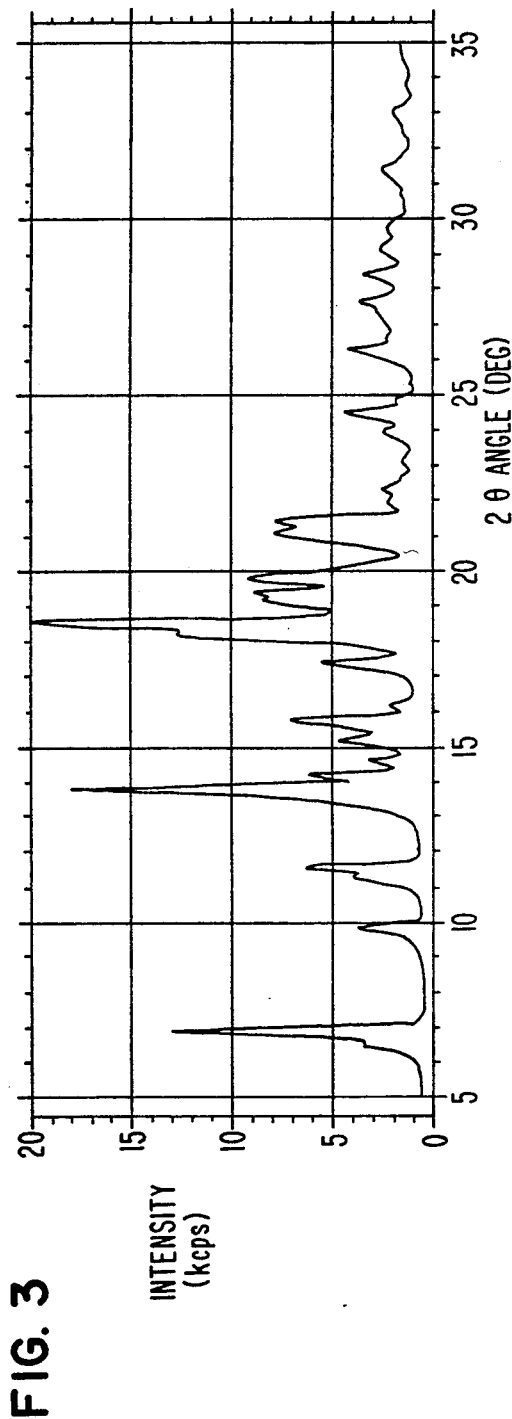
FIG. 3 shows an X ray diffraction spectrum of the compound of the invention as obtained in Example 2.

The present inventors have conducted a number of investigations in search of stable alpha crystals of tetrakis[3-(3,5-di-tert-butyl-4-hydroxyphenyl)propionyloxymethyl]methane and completed the present invention according to which highly pure alpha crystals of tetrakis[3-(3,5-di-tert-butyl-4-hydroxyphenyl)propionyloxymethyl]methane which differ in grain form from the known alpha crystals are provided.

Thus, the invention provides (1) tetrakis[3-(3,5-di-tert-butyl-4-hydroxyphenyl)propionyloxymethyl]methane having the crystal structure of alpha crystals and occurring as granular crystals with good flowability and (2) a method of producing tetrakis[3-(3,5-di-tert-butyl-4-hydroxyphenyl)propionyloxymethyl]methane having the crystal structure of alpha crystals and occurring as granular crystals with good flowability which comprises crystallizing tetrakis[3-(3,5-di-tert-butyl-4-hydroxyphenyl)propionyloxymethyl]methane from a mixed solvent composed of a monohydric alcohol with 1 to 3 carbon atoms and a small amount of water.

The term "granular crystals with good flowability" means crystals that can flow out and drop from containers without adhering to the container wall without particular application of an external force. The grains obtainable according to the invention are rounded and almost free of angles on their surface. It is presumable that, for this reason, the sliding behavior of grains relative to one another be improved and the adhesion to one another be prevented thereby, leading to an improvement in flowability.

The novel alpha crystal form of the compound according to the invention is generally characterized in that crystal grains greater than 1 mm in grain size account for not more than 0.5% by weight, crystal grains 0.1 to 1 mm in grain size for less than 95.5% by weight and crystal grains smaller than 0.1 mm in grain size for less than 4.0% by weight and that the bulk density is not less than 0.35 but less than 0.50.

The raw material tetrakis[3-(3,5-di-tert-butyl-4-hydroxyphenyl)propionyloxymethyl]methane to be used in the production of the novel granular form of tetrakis[3-(3,5-di-tert-butyl-4-hydroxyphenyl)propionyloxymethyl]methane that can be obtained according to the invention and has good flowability may be any of a wide variety of transesterification products having a purity of about 85 to about 90% which result from ordinary transesterification or from transesterification modified with respect to the purity of each starting material for transesterification and/or the charge mole ratio for the purpose of improving the conversion and/or reducing the reaction period, for instance, to give reaction products differing in composition to some extent, or any of currently available commercial products having a high purity of about 96 to about 98%. The method according to the invention thus has the following characteristic features: the addition of a particular compound, as made in the prior art methods, is not necessary; repeated crystallizations, for example formation of an adduct with isopropyl alcohol or the like, separation, drying and recrystallization from methanol and/or ethanol, are not necessary; the presence of a specific amount of the starting material or incompletely esterified product in the reaction product prior to crystallization is not required.

The alcohol solvent having 1 to 3 carbon atoms which is to be used in the crystallization includes methanol, ethanol and isopropanol. When these alcohols are used each singly, and desirable product cannot be obtained, for example a fine powder is formed during crystallization, making stirring difficult and worsening the filterability although stable alpha crystals can be obtained. In view of these facts, the present inventors conceived the idea that a mixed solvent with water should be used. The amount of water to be used should preferably be adjusted to 2 to 10% by weight based on the alcohol. Amounts smaller than 2% by weight tend to give a fine powder while, in amounts greater than 10% by weight, the mixing of the solvent with tetrakis[3-(3,5-di-tert-butyl-4-hydroxyphenyl)propionyloxymethyl]methane in dissolution of the latter with heating becomes incomplete and this may result in a reduced product purity and/or lack of uniformity in grain size. A preferred water content lies within the range of 3 to 9% by weight although it depends on the purity of tetrakis[3-(3,5-di-tert-butyl-4-hydroxyphenyl)propionyloxymethyl]methane prior to crystallization and the solubility of tetrakis[3-(3,5-di-tert-butyl-4-hydroxyphenyl)propionyloxymethyl]methane in the alcohol employed. Such aqueous alcohols are used preferably in an amount of 150 to 200% by weight based on the tetrakis[3-(3,5-di-tert-butyl-4-hydroxyphenyl)propionyloxymethyl]methane prior to crystallization.

Considering the above, the use of 90 to 98% methanol-water is preferred for achieving the object of the invention.

Crystallization is carried out in the following manner. Tetrakis[3-(3,5-di-tert-butyl-4-hydroxyphenyl)propionyloxymethyl]methane prior to crystallization is completely melted by heating to 120° to 130° C. After complete melting, dropwise addition of the crystallization solvent employed is started and the whole amount thereof is added under reflux. After completion of the dropping, it should be confirmed that the contents are clear and transparent. Then the oil bath is removed and, after termination of refluxing, a small amount of alpha crystals are charged as seed crystals. When allowed to cool, the contents begin to become turbid, indicating the start of precipitation of crystals. From this time point, the contents are maintained at a temperature of 60° to 50° C. for about 1.5 to 3 hours for the growth and maturation of crystals. Thereafter, the oil bath is removed and the contents are allowed to cool gradually until the crystal precipitation is complete. The desired product is then recovered by solid-liquid separation.

The purity of tetrakis[3-(3,5-di-tert-butyl-4-hydroxyphenyl)propionyloxymethyl]methane and the use of an aqueous alcohol having an appropriate water content are very important factors for producing highly pure alpha crystals having good flowability in high yields. The temperature and time for the growth and maturation of crystals are also important factors.

The alpha crystals of tetrakis[3-(3,5-di-tert-butyl-4-hydroxyphenyl)propionyloxymethyl]methane as obtained in accordance with the invention differ from the alpha crystals known in the art. They are highly pure and uniform in grain size, with a narrow grain size distribution pattern, and constitute a product composed of rounded grains and having good flowability. Since no hydrocarbon solvent is used, the risk from charging with electricity is minimal. Therefore, the invention greatly contributes to improvement in working environment, to automation and to operability improvement in continuous processing. The crystals can be produced with ease.

The following examples are further illustrative of the present invention. They are, however, by no means limitative of the scope of the invention.

EXAMPLE 1

Figure 7:
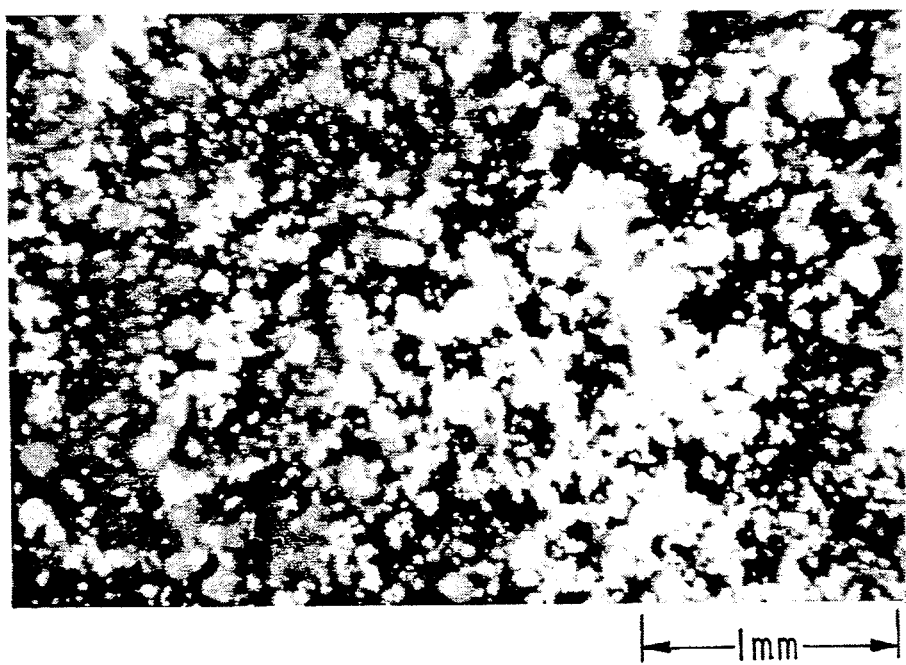
FIG. 7 shows a photomicrograph illustrating the crystal structure of the commercial product available in the market.

The tetrakis[3-(3,5-di-tert-butyl-4-hydroxyphenyl)propionyloxymethyl]methane product commercially available from Ciba-Geigy under the trademark Irganox 1010 has the beta crystal structure as evidenced by its X ray diffraction spectrum shown in FIG. 2 and occurs as a fine powder as evidenced by its photomicrograph illustrative of its crystal structure as shown in FIG. 7.

A 500-ml four-necked flask equipped with stirrer, thermometer, reflux condenser and dropping funnel was charged with 100 g of the fine powder from product mentioned above. The flask inside temperature was raised to 125° C. on an oil bath for complete melting of the product.

Figure 5:
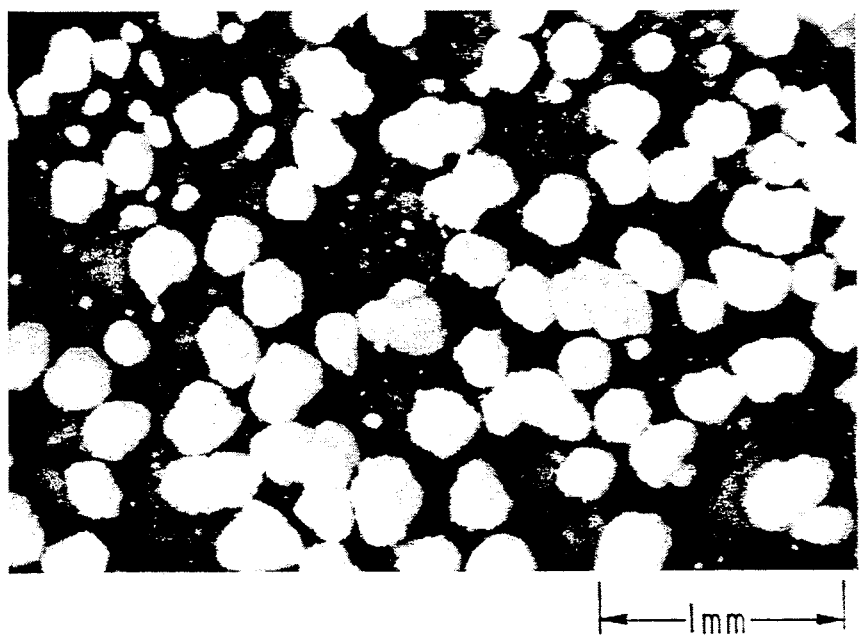
FIG. 5 shows a photomicrograph illustrating the crystal structure of alpha crystals obtainable in accordance with the invention.
Figure 6:
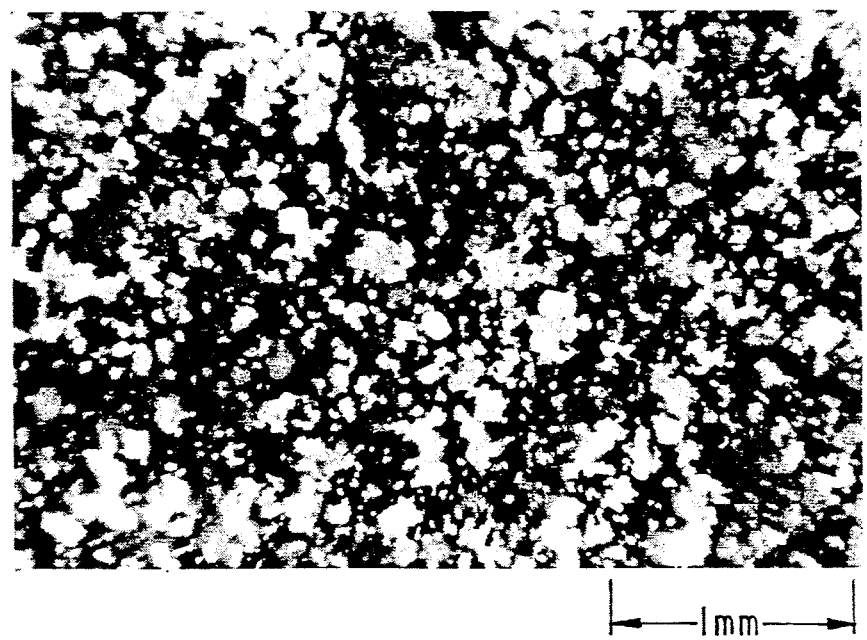
FIG. 6 shows a photomicrograph illustrating the crystal structure of alpha crystals obtainable by the prior art methods.

To this melt was added dropwise gradually 200 g of 95% methanol-water (190 g of methanol plus 10 g of water) over about 20 minutes under reflux, whereupon the inside temperature became about 66 to 68° C. and the contents occurred as a clear solution. The oil bath was removed, the flask contents were allowed to coo and, after refluxing had subsided, a small amount of alpha crystals were added as seed crystals. Immediately after the addition, the flask contents began to become turbid and precipitation of crystals was observed. From this time point, the flask inside temperature was maintained at 50° to 55° C. for 2 hours for crystallization and maturation. The bath was then removed, the flask contents were allowed to cool to 20° C. and, then, solid-liquid separation was performed, followed by drying to give 97.4 g of white crystals with good flowability. These crystals (FIG. 5) had a melting point of 122° to 125° C. and were confirmed to be alpha crystals based on their X ray diffraction spectrum (FIG. 1). The crystal structure of alpha crystals obtained by the conventional methods is shown in FIG. 6.

EXAMPLE 2

A one-liter four-necked flask equipped with stirrer, reflux condenser, thermometer and reduced pressure adjusting valve was charged with 478.5 g of methyl 3-(3,5-di-tert-butyl-4-hydroxyphenyl)propionate, 54.5 g of pentaerythritol and 1.1 g of monobutyltin oxide and the reaction was carried out at 195° C. and atmospheric pressure for 2 hours, while the byproduct methanol was distilled off. The reaction was then continued at 195° C. under reduced pressure (40 mmHg) for 2 hours and further at 195° C. under reduced pressure (2 to 5 mmHg) for 12 hours to drive the reaction to completion, while the byproduct methanol was distilled off. After recovery of atmospheric pressure with nitrogen, the reaction product weighed 483 g and was found to contain 89% of the desired product tetrakis[3-(3,5-di-tert-butyl-4-hydroxyphenyl)propionyloxymethyl]methane as determined by HPLC analysis.

The procedure of Example 1 was followed exactly in the same manner except that 100 g of the above reaction product was used in lieu of 100 g of the fine powder product. White crystals having good flowability were obtained in a yield of 88.1 g.

These crystals had a melting point of 122° to 124° C. Their X ray diffraction spectrum (FIG. 3) confirmed that they were alpha crystals.

COMPARATIVE EXAMPLE 1

Figure 4:
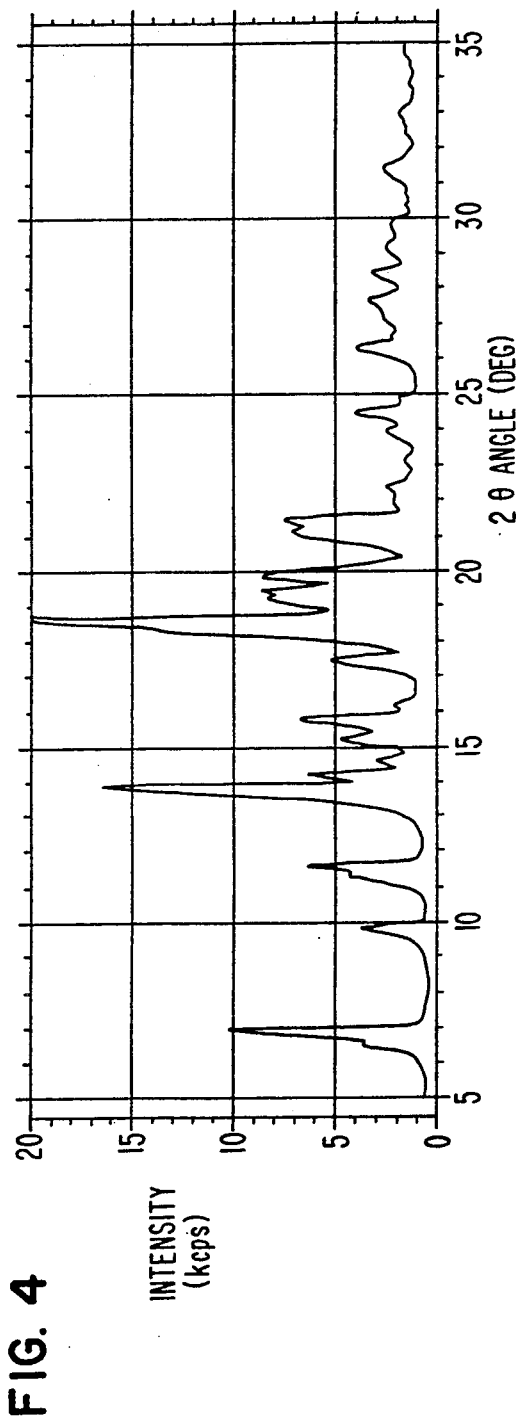
FIG. 4 shows an X ray diffraction spectrum of the compound obtained in Comparative Example 1.

Another 100 g portion of the reaction product obtained in Example 2 was used for crystallization. In this example, 113 g of methanol, the solvent used in Example 1 of Japanese Kokai Tokkyo Koho No. 156646/1985, was used in lieu of 95% methanol-water. A homogeneous solution was prepared by heating to 68° C. and crystallization was effected as described in Example 2. The crystals obtained were washed with 67 ml of cold methanol and dried to give 80 g of a white powder. The crystals had a melting point of 122° to 124° C. and were confirmed to be alpha crystals based on their X ray diffraction spectrum (FIG. 4).

COMPARATIVE EXAMPLE 2

The procedure of Comparative Example 1 was followed in the same manner except that n-heptane, the solvent used in Example 2 of Japanese Patent Publication No. 18617/1967, was used in lieu of methanol. Slightly yellow crystals were obtained. They had a melting point of 118° to 122° C. Based on their X ray diffraction spectrum, it was confirmed that they were alpha crystals.

COMPARATIVE EXAMPLE 3

The procedure of Comparative Example 1 was followed in the same manner except that n-hexane, the solvent used in Example 1 of Japanese Patent Publication No. 19083/1967, was used in lieu of methanol and that the crystallization temperature was 40° C. Slightly yellow crystals were obtained. They had a melting point of 116° to 122° C and, based on their X ray diffraction spectrum, it was confirmed that they were alpha crystals.

The characteristic properties of the crystals obtained in Examples 1 and 2 and Comparative Examples 1 to 3 and of the commercial product are summarized below in Table 1.

TABLE 1

| | Example 1 | Example 2 | Comparative Example 1 | Comparative Example 2 | Comparative Example 3 | Commercial product (note 1) |
|---|---|---|---|---|---|---|
| Crystallization solvent | 95% Methanol-water | 95% Methanol-water | Methanol | n-Heptane | n-Hexane | — |
| Appearance | White crystals | White crystals | White crystals | Slightly yellow crystals | Slightly yellow crystals | White crystalsline powder |
| HPLC purity (%) | 97.6 | 96.8 | 96.5 | 95.2 | 94.6 | 97.0 |
| Melting point (°C.) | 122–125 | 122–124 | 122–125 | 118–122 | 116–122 | 113–114 |
| Crystal structure | Alpha | Alpha | Alpha | Alpha | Alpha | Beta |
| Bulk density (note 2) (g/ml) | 0.39 | 0.40 | 0.28 | 0.30 | 0.33 | 0.35 |
| Angle of repose (note 2) (°) | 41 | 42 | 48 | 51 | 51 | 50 |
| Rate of falling (note 3) (sec/100 ml) | 11 | 12 | 95 | 185 | 200 | 210 |
| Grain size distribution (mm) | | | | | | |
| >1.0 | 0.2 | 0.2 | 4.3 | 0 | 0 | 0.1 |
| 1.0–0.5 | 0.9 | 3.5 | 4.4 | 5.4 | 6.8 | 0.1 |
| 0.5–0.25 | 87.1 | 78.8 | 18.1 | 15.6 | 18.2 | 14.1 |
| 0.25–0.1 | 10.0 | 16.1 | 69.7 | 45.3 | 45.7 | 53.7 |
| <0.1 | 1.8 | 1.4 | 2.9 | 32.7 | 29.3 | 32.0 |

Figure 8:
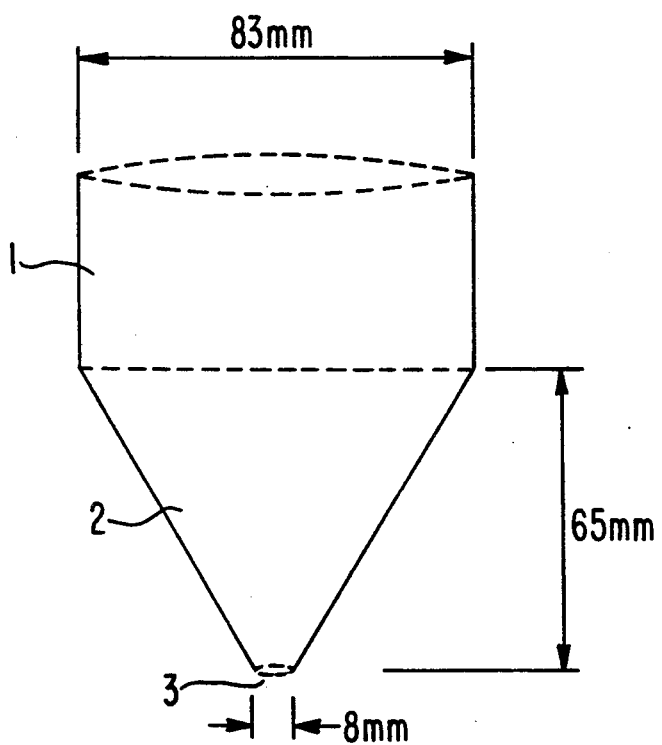
FIG. 8 shows the hopper used in measuring the rate of falling.

Note 1: Ciby Geigy's Irganox 1010 (Registered Trademark)
Note 2: Measured on a Hosokawa Micron powder tester.
Note 3: Rate of falling from a hopper (FIG. 8). (The smaller the value is, the better the flowability is.)

We claim:

1. Tetrakis[3-(3,5-di-tert-butyl-4-hydroxyphenyl)propionyloxymethyl]methane having a crystal structure of alpha crystals and occurring as granular crystals with good flowability, wherein crystal grains greater than 1 mm in grain size account for not more than 0.5% by weight of said granular crystals, crystal grains 0.1 to 1 mm in grain size account for not less than 95.5% by weight of said granular crystals, and crystal grains smaller than 0.1 mm in grain size account for less than 4.0% by weight of said granular crystals, and the bulk density of said granular crystals being not less than 0.35 but less than 0.50.

2. A method of producing tetrakis[3-(3,5-di-tert-butyl-4-hydroxyphenyl)propionyloxymethyl]methane having a crystal structure of alpha crystals and occurring as granular crystals with good flowability, wherein crystal grains greater than 1 mm in grain size account for not more than 0.5% by weight of said granular crystals, crystal grains 0.1 to 1 mm in grain size account for not less than 95.5% by weight of said granular crystals, and crystal grains smaller than 0.1 mm in grain size account for less than 4.0% by weight of said granular crystals, and the bulk density of said granular crystals being not less than 0.35 but less than 0.50, which comprises crystallizing tetrakis[3-(3,5-di-tert-butyl-4-hydroxyphenyl)propionyloxymethyl]methane from a solution containing tetrakis[3-(3,5-tert-butyl-4-hydroxyphenyl)propionyloxymethyl]methane having a purity of about 85% or more and a mixed solvent, the mixed solvent composed of a monohydric alcohol having 1 to 3 carbon atoms and water in an amount of 2 to 10% by weight based upon the monohydric alcohol, and maintaining the crystallized products at a temperature of 50°–60° C. for 1.5 to 3 hours for growth and maturation of the crystals.

3. The method of claim 2, wherein the mixed solvent is 90 to 98% methanol-water.